United States Patent [19]

Frank

[11] Patent Number: 5,087,770
[45] Date of Patent: Feb. 11, 1992

[54] ISOPROPYL TETRAMETHYL AND PENTAMETHYL INDANE MUSKS

[75] Inventor: Walter C. Frank, Holland, Pa.

[73] Assignee: Union Camp Corporation, Wayne, N.J.

[21] Appl. No.: 621,697

[22] Filed: Dec. 3, 1990

[51] Int. Cl.⁵ ............................................. C07C 49/215
[52] U.S. Cl. ................................... 568/327; 568/340; 512/17
[58] Field of Search .................. 568/327, 440; 512/17

[56] References Cited

U.S. PATENT DOCUMENTS

| | | | |
|---|---|---|---|
| 3,045,047 | 7/1962 | Davidson et al. | 568/327 |
| 3,509,215 | 4/1970 | Wood et al. | 568/327 |
| 4,352,748 | 10/1982 | Traas et al. | 568/327 |
| 4,466,908 | 8/1984 | Sprecker et al. | 512/17 |
| 4,767,882 | 8/1988 | Suzukamo et al. | 512/17 |
| 4,908,349 | 3/1990 | Gangenbach | 512/17 |

OTHER PUBLICATIONS

Fehr et al., Helv. Chem. Acta, vol. 72, pp. 1537-53 (1989).

Primary Examiner—James H. Reamer
Attorney, Agent, or Firm—William K. Wissing

[57] ABSTRACT

Novel acylated tetramethyl and pentamethyl isopropyl indane compounds having a fragrant musk-like aroma are disclosed.

24 Claims, No Drawings

ISOPROPYL TETRAMETHYL AND PENTAMETHYL INDANE MUSKS

BACKGROUND OF THE INVENTION

The present invention relates to novel acylated tetramethyl and pentamethyl isopropyl indane compounds having a fragrant musk-like aroma.

Musk fragrances are in great demand for use in various products such as in perfumes, colognes, cosmetics, soaps and others. However, natural musk, which is obtained from the Asian musk deer, is extremely scarce and is quite expensive. Accordingly, fragrance chemists have spent considerable time searching for synthetic products which duplicate or closely simulate this natural musk scent.

As a result of these research efforts, a number of different synthetic musks have been discovered. Among such synthetic compounds are the acetyl indanes described by U.S. Pat. No. 4,466,908, compounds of the formulas

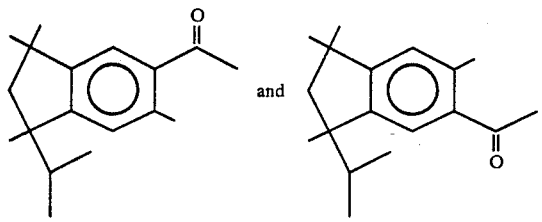

which may be employed, if desired, in combination with acetyl tetrahydronaphthalenes of the formula

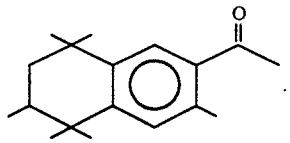

Similarly, Fehr et al., *Helvetica Chimica Acta*, Vol. 72, pp. 1537-1553 (1989) discusses such synthetic musks as those of the formula

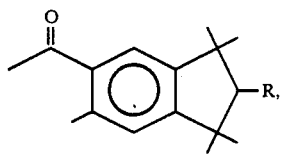

wherein R is either H or $CH_3$, which structures were originally elucidated by Weber et al., *Rec. Trav. Chem.*, Vol. 74, pp. 1179-1196 (1955).

U.S. Pat. No. 4,352,748 discloses formylated and acetylated indane musks, including those of the formulas

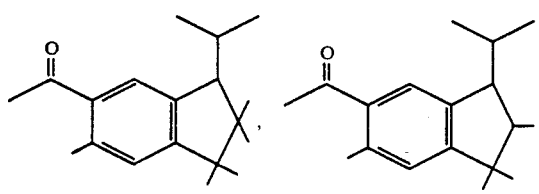

and

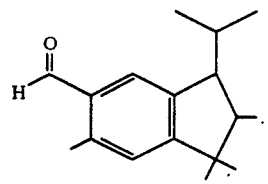

Acetyl indanes, such as 6-acetyl-1,1,3,3,5-pentamethylindane, 5-acetyl-1,1,2,3,3-pentamethylindane and 6-acetyl-5-ethyl-1,1,2,3,3-pentamethylindane, are disclosed in French Patent No. 1,392,804 (as reported in Chemical Abstracts, Vol. 63, p. 1681d (1965)).

European Patent Publication 0 301 375 A2 describes formylated tetralins, such as 1,1,2,4,4-pentamethyl-6-formyl-1,2,3,4-tetrahydronaphthalene, and their utility as synthetic musks.

New and or better musk aroma compounds are needed. The present invention is directed to this important end.

SUMMARY OF THE INVENTION

The present invention provides novel indane compounds of the formula:

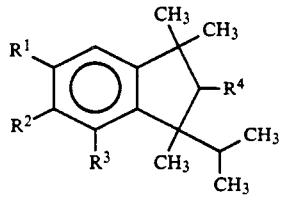

wherein
$R^1$ is H, $CH_3$, CHO, or $CH_3CO$;
$R^2$ is H, $CH_3$, CHO, and $CH_3CO$;
$R^3$ is H, or $CH_3$; and
$R^4$ is H, or $CH_3$;
provided that
(i) one of $R^1$ or $R^2$ is CHO, or $CH_3CO$;
(ii) one of $R^1$ or $R^2$ is H, or $CH_3$;
(iii) when $R^3$ and $R^4$ are both H, $R^1$ and $R^2$ are other than $CH_3CO$; and
(iv) when $R^1$ and $R^3$ are both $CH_3$, $R^2$ is CHO.

The formula [I] compounds include those compounds wherein:
$R^1$ is CHO, $R^2$ is $CH_3$, $R^3$ is H, and $R^4$ is H;
$R^1$ is CHO, $R^2$ is $CH_3$, $R^3$ is H, and $R^4$ is $CH_3$;
$R^1$ is CHO, $R^2$ is $CH_3$, $R^3$ is $CH_3$, and $R^4$ is H;
$R^1$ is CHO, $R^2$ is $CH_3$, $R^3$ is $CH_3$, and $R^4$ is $CH_3$;
$R^1$ is CHO, $R^2$ is H, $R^3$ is H, and $R^4$ is H;
$R^1$ is CHO, $R^2$ is H, $R^3$ is H, and $R^4$ is $CH_3$;
$R^1$ is CHO, $R^2$ is H, $R^3$ is $CH_3$, and $R^4$ is H;
$R^1$ is CHO, $R^2$ is H, $R^3$ is H, and $R^4$ is $CH_3$;
$R^1$ is $CH_3CO$, $R^2$ is $CH_3$, $R^3$ is $CH_3$, and $R^4$ is H;
$R^1$ is $CH_3CO$, $R^2$ is $CH_3$, $R^3$ is $CH_3$, and $R^4$ is $CH_3$;
$R^1$ is $CH_3CO$, $R^2$ is H, $R^3$ is $CH_3$, and $R^4$ is H;
$R^1$ is $CH_3CO$, $R^2$ is H, $R^3$ is $CH_3$, and $R^4$ is $CH_3$;
$R^1$ is $CH_3CO$, $R^2$ is H, $R^3$ is H, and $R^4$ is $CH_3$;
$R^1$ is $CH_3CO$, $R^2$ is $CH_3$, $R^3$ is H, and $R^4$ is $CH_3$;
$R^1$ is $CH_3$, $R^2$ is CHO, $R^3$ is H, and $R^4$ is H;
$R^1$ is $CH_3$, $R^2$ is CHO, $R^3$ is H, and $R^4$ is $CH_3$;
$R^1$ is $CH_3$, $R^2$ is CHO, $R^3$ is $CH_3$, and $R^4$ is H;

$R^1$ is $CH_3$, $R^2$ is CHO, $R^3$ is $CH_3$, and $R^4$ is $CH_3$;
$R^1$ is H, $R^2$ is CHO, $R^3$ is H, and $R^4$ is H;
$R^1$ is H, $R^2$ is CHO, $R^3$ is H, and $R^4$ is $CH_3$;
$R^1$ is H, $R^2$ is CHO, $R^3$ is $CH_3$, and $R^4$ is H;
$R^1$ is H, $R^2$ is CHO, $R^3$ is $CH_3$, and $R^4$ is $CH_3$;
$R^1$ is H, $R^2$ is CHO, $R^3$ is $CH_3$, and $R^4$ is H;
$R^1$ is H, $R^2$ is $CH_3CO$, $R^3$ is $CH_3$, and $R^4$ is H;
$R^1$ is H, $R^2$ is $CH_3CO$, $R^3$ is $CH_3$, and $R^4$ is $CH_3$;
$R^1$ is H, $R^2$ is $CH_3CO$, $R^3$ is H, and $R^4$ is $CH_3$; and
$R^1$ is $CH_3$, $R^2$ is $CH_3CO$, $R^3$ is H, and $R^4$ is $CH_3$.

The foregoing compounds are active musk aroma fragrances having utility in the perfumery and/or other industries. The compounds of the invention can be used alone or in combination with indane and tetrahydronaphthalene isomers thereof, and/or in combination with other compounds or ingredients.

DETAILED DESCRIPTION OF THE INVENTION

The novel tetramethyl and pentamethyl isopropyl indane compounds of the invention can be prepared in various fashions. Preferably, however, the compounds are prepared by isomerizing a tetrahydronaphthalene compound of the formula

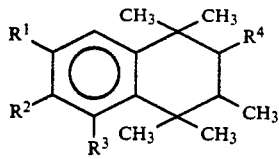   [II]

wherein, in formula [II], $R^1$, $R^2$, $R^3$, and $R^4$ are, independently, H, or $CH_3$, in the presence of a Lewis acid, a solvent which can be a halogenated or unhalogenated solvent and, optionally, a phase transfer agent, said Lewis acid being present in an amount of less than about 50 mole percent based on the amount of the tetrahydronaphthalene compound of the formula [II], to produce the corresponding indane compound of the formula

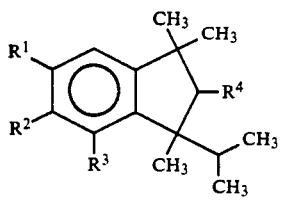   [III]

wherein in formula [III], $R^1$, $R^2$, $R^3$, and $R^4$ are, independently, H, or $CH_3$. The foregoing process, which is disclosed in my copending U.S. patent application, entitled "Processes For Preparing Alkylated Indanes and Tetrahydronaphthalenes", 07/621,688, filed concurrently herewith, the disclosures of which are hereby incorporated herein by reference in their entirety, will produce the formula [III] compounds at a high rate of reaction, using better, safer, more convenient or less expensive process methodology than many processes known heretofore. As those skilled in the art will recognize once armed with the present disclosure, the formula [III] compounds can also be prepared in other fashions, such as using the processes described in U.S. Patent Nos. 4,466,908 and 4,551,573, the disclosures of which are incorporated herein by reference in their entirety.

The formula [III] compounds can then be formylated (that is, the H of $R^1$ or $R^2$ is converted to CHO), oxidized (that is, the $CH_3$ of $R^1$ or $R^2$ is converted to CHO), or acetylated (that is, the H of $R^1$ or $R^2$ is converted to $CH_3CO$), the foregoing being carried out using conventional acylation or benzylic oxidation technology, to produce the formula [I] compounds of the invention.

As noted above, in accordance with the preferred preparation route, the compounds represented by formula [III] can be synthesized by contacting a corresponding tetrahydronaphthalene compound of formula [II] with less than about 50 mole percent of a Lewis acid based on the amount of the tetrahydronaphthalene compound of formula [II], in the presence of a solvent which can be a halogenated or unhalogenated solvent. Optionally, the process is carried out in the additional presence of a phase transfer agent.

In preferred embodiments, the formula [II] compounds are 1,1,3,4,4,6-hexamethyl-1,2,3,4-tetrahydronaphthalene (HMT), that is, a compound of formula [II] wherein $R^1$ is H, $R^2$ is $CH_3$, $R^3$ is H, and $R^4$ is H, and/or 1,1,2,4,4,6-hexamethyl-1,2,3,4-tetrahydronaphthalene, that is, a compound of formula [II] wherein R is $CH_3$, $R^2$ is H, $R^3$ is H, and $R^4$ is H. The preferred formula [III] compounds resulting from the isomerization of the foregoing preferred formula [II] compounds are 1,1,3,5-tetramethyl-3-isopropylindane (IPI), that is, a compound of formula [II] wherein $R^1$ is H, $R^2$ is $CH_3$, $R^3$ is H, and $R^4$ is H, and/or 1,3,3,5-tetramethyl-1-isopropylindane, that is, a compound of formula [II] wherein $R^1$ is $CH_3$, $R^2$ is H, $R^3$ is H, and $R^4$ is H.

The tetrahydronaphthalene formula [II] starting materials for the foregoing process may be prepared from readily available reagents using various published processes, such as those disclosed in U.S. Pat. Nos. 4,877,910, 4,877,911, 4,877,912, 4,877,913, 4,877,914, 4,877,915 and 4,877,916. Other processes for the preparation of tetrahydronaphthalene starting materials include U.S. Pat. Nos. 3,856,875, 3,246,044, 4,284,818, 3,379,785 and 4,551,573, Japanese Patent Publication SHO 57-40420, and Fehr et al., *Helvetica Chimica Acta*, Vol. 72, pp. 1537–1553 (1989), as well as others. The disclosures of each of the foregoing patents and publications are incorporated herein by reference in their entirety.

Any of the Lewis acids, that is, any non-protonic compounds capable of accepting an electron pair, are suitable for use in the foregoing preferred preparatory process. Exemplary Lewis acids include metal halides such as aluminum halides (including aluminum chloride, aluminum bromide, aluminum iodide, monofluorodichloroaluminum, monobromodichloroaluminum and monoiododichloroaluminum. Alkyl metals and alkyl metal halides suitable for use as Lewis acids in the process are disclosed, for example, in Kennedy, Joseph P., *Carbocationic Polymerization*, p. 221 (Wiley-Interscience Publishers, 1982), the disclosures of which are incorporated herein by reference. In the foregoing process, aluminum halides are preferred. Of the aluminum halides, aluminum chloride and aluminum bromide, particularly aluminum chloride ($AlCl_3$), are most preferred.

In accordance with the foregoing process, the Lewis acid is present in an amount less than about 50 mole percent based on the amount of the tetrahydronaphthalene compound charged. Preferably the Lewis acid is present in an amount less than about 40 mole percent, more preferably less than about 30 mole percent, even more preferably less than about 20 mole percent, and most preferably is present in an amount equal to about 10 mole percent, all based on the amount of the tetrahydronaphthalene compound starting material.

Halogenated solvents suitable for use in the preferred process are varied, and include halogenated aliphatic halogenated alicyclic and halogenated aromatic hydrocarbon solvents. Particularly preferred are the halogenated aliphatic hydrocarbons. Suitable halogenated solvents include, for example, 1,2-dichloroethane, 1,1-dichloroethane, trichloromethane, dichloroethane, dichloromethane, 1,1,2,2-tetrachloroethylene, 1,2-dichloroethylene, 1,2,3-trichloropropane, 1,1,2-trichloroethane, monochlorobenzene, fluorobenzene, and orthodichlorobenzene. Particularly preferred halogenated solvents include dichloromethane, trichloromethane and 1,2-dichloroethane.

As an alternative to or in combination with the halogenated solvents, one may employ unhalogenated solvents. A variety of unhalogenated solvents may be utilized in the process, including, unhalogenated aliphatic, unhalogenated alicyclic and unhalogenated aromatic hydrocarbon solvents. Such unhalogenated solvents are generally preferred over the halogenated solvents for reasons of safety. Particularly preferred are the unhalogenated aliphatic and unhalogenated alicyclic hydrocarbons. Suitable unhalogenated solvents include, for example, the aliphatic hydrocarbon solvents n-hexane, n-heptane and n-octane, the alicyclic hydrocarbon solvent cyclohexane, and aromatic hydrocarbon solvents, such as mesitylene. A particularly preferred unhalogenated solvent is the unhalogenated alicyclic hydrocarbon solvent cyclohexane.

Phase transfer agents suitable for use in the preparatory process include onium salts such as ammonium, phosphonium and sulfonium salts. Other phase transfer agents suitable for use will be readily apparent to those skilled in the art, once having been made aware of the present disclosure.

Examples of ammonium phase transfer agents include quaternary ammonium halides such as methyltrioctylammonium chloride, methyltrinonylammonium chloride, methyltridecylammonium chloride, hexadecyltrihexylammonium bromide, ethyltrioctylammonium bromide, didodecyldimethylammonium chloride, tetraheptylammonium iodide, dioctadecyldimethylammonium chloride, tridecylbenzylammonium chloride, and homologues thereof having chlorine, fluorine, bromine or iodine atoms substituted for the enumerated halide atom.

Exemplary phosphonium phase transfer agents include quaternary phosphonium halide such as tributyldecylphosphonium iodide, triphenyldecylphosphonium iodide, tributylhexadecylphosphonium iodide, and homologues thereof having chlorine, fluorine or bromine atoms substituted for the iodine atom.

Representative sulfonium phase transfer agents include ternary sulfonium halides such as lauryldimethylsulfonium iodide, lauryldiethylsulfonium iodide and tri(n-butyl)sulfonium iodide, and homologues thereof having chlorine, fluorine or bromine atoms substituted for the iodine atom.

These and other suitable phase transfer agents are described, for example, in Napier et al., U.S. Pat. No. 3,992,432 entitled "Phase Transfer Catalysis of Heterogeneous Reactions by Quaternary Salts", and in Kondo et al., *Synthesis*, pp. 403–404 (May 1988), the disclosures of which are incorporated herein by reference.

Preferable phase transfer agents are ammonium or sulfonium salts, particularly quaternary ammonium or ternary sulfonium halides. Most preferred are quaternary ammonium halides, particularly methyltrioctylammonium chloride, and a mixture of methyltrioctylammonium chloride and methyltridecylammonium chloride. The latter mixture is marketed under the trademark Adogen-464, by Sherex Co., located in Dublin, Ohio.

In general, the molar proportions of the reagents employed in the present preferred preparatory process can be varied over a relatively wide range, provided that the Lewis acid is present in an amount of less than about 50 mole percent based on the amount of the tetrahydronaphthalene compound starting material. As previously noted, it is preferable that the Lewis acid be present in an amount of less than about 40 mole percent, more preferably less than about 30 mole percent, even more preferably less than about 20 mole percent, and most preferably in an amount equal to about 10 mole percent, all based on the amount of tetrahydronaphthalene starting material. Of course within these parameters, the amount of Lewis acid will depend in part on the particular solvent employed, the presence or absence of a phase transfer agent, and the specific tetrahydronaphthalene starting material and other reaction conditions such as time, temperature, pressure, etc. The particular amount to be employed will be well within the ambit of those skilled in the art, once armed with the present disclosures.

It has been surprisingly found, however, that it is helpful to minimize the amount of solid Lewis acid catalyst present in the reaction medium. As an important feature in accomplishing this goal, the amount of the Lewis acid must be kept reasonably low, that is, the amount should be kept below about 50 mole percent based on the amount of the tetrahydronaphthalene starting material, as previously described. Also helpful in minimizing the amount of said Lewis acid catalyst present in the reaction medium is the use of a phase transfer agent and/or a solvent. Such phase transfer agents and solvents will assist in liquefying and/or solubilizing the Lewis acid catalyst. Indeed, it has been surprisingly found that the existence of an excess of solid Lewis acid catalyst such as that urged in Sprecker et al. U.S. Pat. No. 4,466,908, fails to serve any beneficial chemical purpose in such reactions. In fact, the presence of excess solid catalyst is detrimental in that it leads to greater reactor corrosion problems, less uniform reaction rates, various chemical engineering difficulties, and poses environmental concerns. Contrary to the suggestions in Sprecker et al., the foregoing preferred preparatory reaction proceeds rapidly and efficiently to yield the desired compounds of formula [III].

Although varying amounts of the other process constituents can be employed, for best results, however, it is important to maintain a ratio of less than one mole of phase transfer gent per mole of Lewis acid. Preferably, the molar ratio is about 0.8 to 1.0, more preferably about 0.5 to 1.0, phase transfer agent to Lewis acid. It should be noted that some phase transfer agents sold commercially are sold in an impure form. Such impurities usually comprise water or an alcohol species. Water and alcohol, as well as other impurities, will react adversely with the Lewis acid, thereby lowering the amount of Lewis acid available for the preparatory process. Accordingly, where the phase transfer agent added contains such impurities, the amount of Lewis acid should be increased to account for these impurities. In such a situation, the ratio of transfer agent to Lewis acid might be about 0.3 to 1.0. Such impure agent-containing mixtures are referred to herein as mixtures in an "impure form".

The isomerization reaction can be carried out in any suitable vessel which provides sufficient contacting between the Lewis acid, the phase transfer agent and the other reactants. For simplicity, a stirred batch reactor can be employed. Although stirring is recommended to provide efficient contact between reactants, it has been found that in the phase transfer agent and/or solvent, the Lewis acid is able to solubilize rather quickly, thereby obviating the need for stringent stirring requirements. The reaction vessel used should be resistant to the possible corrosive nature of the Lewis acid. Glass-lined vessels are suitable for this purpose, as well as other vessel materials well-known in the art.

The reagents may be added to the vessel in any order, although generally the solvent, the tetrahydronaphthalene compound, and any phase transfer agent are added first, followed by Lewis acid addition.

Ideally, the reaction is carried out at temperatures ranging from about −30° C. to about 50° C., preferably temperatures ranging from about −10° C. to about 30° C., and most preferably at temperatures ranging from about 0° C. to about 20° C.

The pressure at which the reaction is carried out is not critical. If the reaction is carried out in a sealed vessel, autogenous pressure is acceptable, although higher or lower pressure, if desired, may be employed. The reaction may also be carried out at atmospheric pressure in an open reaction vessel, in which case, the vessel is preferably equipped with a moisture trap to prevent significant exposure of Lewis acid to moisture. The reaction may take place in an oxygen atmosphere or an inert atmosphere, as in the presence of a gas such as nitrogen, argon and the like, the type of atmosphere also not being critical.

Reaction time is generally rather short and is often dictated by the type of equipment employed. Sufficient time should be provided, however, for thorough contacting of the tetrahydronaphthalene compound, the Lewis acid, the solvent, and any phase transfer employed. Generally, the isomerization reaction proceeds to equilibrium in about 1 to about 8 hours.

As those skilled in the art would recognize, simple methyl migrations from one aromatic ring carbon to another within an aromatic nucleus can occur when Friedel-Crafts-type conditions are employed. Thus, for example, when HMT is employed as the starting material in the subject process, migration of a methyl group from its original $R^2$ position in formula [II] to the $R^1$ position in that formula before isomerization to the corresponding indane of formula [III] can result in a reaction product mixture containing not only HMT and IPI, but a mixture which will generally contain also 1,1,2,4,4,6-hexamethyl-1,2,3,4-tetrahydronaphthalene and 1,3,3,5-tetramethyl-1-isopropylindane. Similarly, migration of a methyl group in the IPI product following isomerization can result in a reaction product mixture containing again not only HMT and IPI, but a mixture which will generally contain also 1,1,2,4,4,6-hexamethyl-1,2,3,4-tetrahydronaphthalene and 1,3,3,5-tetramethyl-1-isopropylindane. The compound resulting from the methyl migration phenomenon is referred to herein as the methyl migrated version of the original compound.

Product can be recovered from the reaction mixture by first quenching the reaction mixture in cold water or on crushed ice, preferably on ice, and then processing the mixture in the usual manner for Friedel-Crafts reactions to extract the desired indane compounds. Suitable extraction protocol is described, for example, in *Friedel-Crafts Reactions*. Typically, following quenching and the resultant phase separation, the organic layer is washed an additional time with water to aid in removal of the Lewis acid. One or more additional washings can be carried out with dilute alkali solution to further aid Lewis acid removal. The resultant product is generally a mixture of the tetrahydronaphthalene starting material, any methyl migrated versions thereof, any indane isomerates, and any methyl migrated versions thereof, such a mixture collectively referred to herein as a crude product mixture. Product of varying degrees of purification can then be obtained by subjecting the washed reaction mixture to fractional crystallization, reduced pressure fractional distillation, commercial chromatographic separation, combinations thereof, or other separation means well known to those skilled in the art.

The formula [III] indane compounds prepared in accordance with the foregoing processes, whether purified, partially purified, or as a crude product mixture (that is, a mixture of the tetrahydronaphthalene starting material, any methyl migrated versions thereof, any indane isomerates and any methyl migrated versions thereof), are then oxidized or acylated to obtain formylated and acetylated tetramethyl and pentamethyl isopropyl indane compounds of formula [I], or compositions containing such compounds, having very fine, musk-like fragrances, a characteristic which renders them highly valuable for use in the perfumery industry.

Specifically, to produce the formylated or acetylated compounds of the invention, that is, compounds where $R^1$ or $R^2$ is CHO (a formyl substituted) or $R^1$ or $R^2$ is $CH_3CO$ (an acetyl substituent), conventional acylation or benzylic oxidation process methodology is employed. The acylation process may be carried out using conventional methods, such as by reacting the isopropyl indane compounds or compositions containing such compounds with an acyl halide or acid anhydride in the presence of an acid-acting catalyst. Such acylation methods are well known in the art and are described, for example, in U.S. Pat. No. 4,184,818, the disclosures of which are incorporated herein by reference, in their entirety. Suitable acylation methodology is also described, for example, in *Organic Synthesis*, Collective Vol. 5, pp. 49–50 (John Wiley & Sons, 1973) (in the case of formylation), and U.S. Pat. Nos. 4,446,908, 4,352,748, 2,752,404, 2,759,022, and 2,851,501 (in the case of acetylation), the disclosures of each of which are incorporated herein by reference, in their entirety. The benzylic oxidation process may be carried out using conventional methods, such as by reacting the isopropyl indane compounds or compositions with chromyl chloride, activated manganese dioxide or ceric ammonium nitrate. Such oxidation methods are well known in the art and are described, for example, in European Patent Publication 301,375, the disclosures of which are incorporated herein by reference in their entirety.

Where purified product is acylated or oxidized, the resultant product is a compound of the formula:

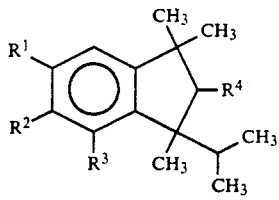

[I]

wherein
R$^1$ is H, CH$_3$, CHO, or CH$_3$CO;
R$^2$ is H, CH$_3$, CHO, and CH$_3$CO;
R$^3$ is H, or CH$_3$; and
R$^4$ is H, or CH$_3$;
provided that
(i) one of R$^1$ or R$^2$ is CHO, or CH$_3$CO;
(ii) one of R$^1$ or R$^2$ is H, or CH$_3$;
(iii) when R$^3$ and R$^4$ are both H, R$^1$ and R$^2$ are other than CH$_3$CO; and
(iv) when R$^1$ and R$^3$ are both CH$_3$, R$^2$ is CHO.

The formula [I] compounds include those compounds wherein:

R$^1$ is CHO, R$^2$ is CH$_3$, R$^3$ is H, and R$^4$ is H;
R$^1$ is CHO, R$^2$ is CH$_3$, R$^3$ is H, and R$^4$ is CH$_3$;
R$^1$ is CHO, R$^2$ is CH$_3$, R$^3$ is CH$_3$, and R$^4$ is H;
R$^1$ is CHO, R$^2$ is CH$_3$, R$^3$ is CH$_3$, and R$^4$ is CH$_3$;
R$^1$ is CHO, R$^2$ is H, R$^3$ is H, and R$^4$ is H;
R$^1$ is CHO, R$^2$ is H, R$^3$ is H, and R$^4$ is CH$_3$;
R$^1$ is CHO, R$^2$ is H, R$^3$ is CH$_3$, and R$^4$ is H;
R$^1$ is CHO, R$^2$ is H, R$^3$ is CH$_3$, and R$^4$ is CH$_3$;
R$^1$ is CH$_3$CO, R$^2$ is CH$_2$, R$^3$ is CH$_3$, and R$^4$ is H;
R$^1$ is CH$_3$CO, R$^2$ is CH$_2$, R$^3$ is CH$_3$, and R$^4$ is CH$_3$;
R$^1$ is CH$_3$CO, R$^2$ is H, R$^3$ is CH$_3$, and R$^4$ is H;
R$^1$ is CH$_3$CO, R$^2$ is H, R$^3$ is CH$_3$, and R$^4$ is CH$_3$;
R$^1$ is CH$_3$CO, R$^2$ is H, R$^3$ is H, and R$^4$ is CH$_3$;
R$^1$ is CH$_3$CO, R$^2$ is CH$_3$, R$^3$ is H, and R$^4$ is CH$_3$;
R$^1$ is CH$_3$, R$^2$ is CHO, R$^3$ is H, and R$^4$ is H;
R$^1$ is CH$_3$; R$^2$ is CHO, R$^3$ is H, and R$^4$ is CH$_3$;
R$^1$ is CH$_3$, R$^2$ is CHO, R$^3$ is CH$_3$, and R$^4$ is H;
R$^1$ is CH$_3$, R$^2$ is CHO, R$^3$ is CH$_3$, and R$^4$ is CH$_3$;
R$^1$ is H, R$^2$ is CHO, R$^3$ is H, and R$^4$ is H;
R$^1$ is H, R$^2$ is CHO, R$^3$ is H, and R$^4$ is CH$_3$;
R$^1$ is H, R$^2$ is CHO, R$^3$ is CH$_3$, and R$^4$ is H;
R$^1$ is H, R$^2$ is CHO, R$^3$ is CH$_3$, and R$^4$ is CH$_3$;
R$^1$ is H, R$^2$ is CH$_3$CO, R$^3$ is CH$_3$, and R$^4$ is H;
R$^1$ is H, R$^2$ is CH$_3$CO, R$^3$ is CH$_3$, and R$^4$ is CH$_3$;
R$^1$ is H, R$^2$ is CH$_3$CO, R$^3$ is H, and R$^4$ is CH$_3$;
R$^1$ is CH$_3$, R$^2$ is CH$_3$CO, R$^3$ is H, and R$^4$ is CH$_3$;

and the present invention is directed to such compounds within the scope of formula [I].

Where the crude product mixture is acylated or oxidized, the resultant product is a mixture of compounds that generally includes tetrahydronaphthalene starting materials in formylated or acetylated form, any methyl migrated versions of the formylated or acetylated tetrahydronaphthalene starting materials, any indane isomerates in formylated or acetylated form, and any methyl migrated versions of the formylated or acetylated indane isomerates, and the present invention also encompasses such formylated or acetylated mixtures of compounds. The formylated or acetylated tetrahydronaphthalene compounds and any methyl migrated versions thereof, referred to above as present in the mixture, are compounds of the formula:

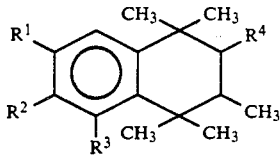

[IV]

wherein
R$^1$ is H, CH$_3$, CHO, or CH$_3$CO;
R$^2$ is H, CH$_3$, CHO, or CH$_3$CO;
R$^3$ is H, or CH$_3$; and
R$^4$ is H, or CH$_3$;
provided that
(i) one of R$^1$ or R$^2$ is CHO or CH$_3$CO;
(ii) one of R$^1$ or R$^2$ is H or CH$_3$;
(iii) when R$^3$ and R$^4$ are both H, R$^1$ and R$^2$ are other than CH$_3$CO; and
(iv) when R$^1$ and R$^3$ are both CH$_3$, R$^2$ is CHO.

The formylated or acetylated indane isomerates and any methyl migrated versions thereof, referred to above as present in the mixture, are the compounds of formula [I]. As one skilled in the art, armed with the present disclosure, would recognize, the specific mixtures obtained are dependent upon which of the particular tetrahydronaphthalene starting materials of formula [II] are employed. In view of the various starting materials available within the constraints of formula [II], the specific mixtures would include, for example, mixtures with the following predominant components:

compositions comprising the compounds of formula [I] wherein R$^1$ is CHO, R$^2$ is CH$_3$, R$^3$ is H, and R$^4$ is H, and R$^1$ is CH$_3$, R$^2$ is CHO, R$^3$ is H, and R$^4$ is H, and the compounds of formula [IV] wherein R$^1$ is CHO, R$^2$ is CH$_3$, and R$^3$ is H, and R$^4$ is H, and R$^1$ is CH$_3$, R$^2$ is CHO, R$^3$ is H, and R$^4$ is H;

compositions comprising the compounds of formula [I] wherein R$^1$ is CHO, R$^2$ is CH$_3$, R$^3$ is H, and R$^4$ is CH$_3$, and R$^1$ is CH$_3$, R$^2$ is CHO, R$^3$ is H, and R$^4$ is CH$_3$, and the compounds of formula [IV] wherein R$^1$ is CHO, R$^2$ is CH$_3$, and R$^3$ is H, and R$^4$ is CH$_3$, and R$^1$ is CH$_3$, R$^2$ is CHO, R$^3$ is H, and R$^4$ is CH$_3$;

compositions comprising the compounds of formula [I] wherein R$^1$ is CHO, R$^2$ is CH:, R$^3$ is CH$_3$, and R$^4$ is H, and R$^1$ is CH$_3$, R$^2$ is CHO, R$^3$ is CH$_3$, and R$^4$ is H, and the compounds of formula [IV] wherein R$^1$ is CHO, R$^2$ is CH$_3$, R$^3$ is CH$_3$, and R$^4$ is H, and R$^1$ is CH$_3$, R$^2$ is CHO, R$_3$ is CH$_3$, and R$^4$ is H;

compositions comprising the compounds of formula [I] wherein R$^1$ is CHO, R$^2$ is CH$_3$, R$^3$ is CH$_3$, and R$^4$ is CH$_3$, and R$^1$ is CH$^3$, R$^2$ is CHO, R$^3$ is CH$_3$, and R$^4$ is CH$_3$, and the compounds of formula [IV] wherein R$^1$ is CHO, R$^2$ is CH$_3$, R$^3$ is CH$_3$, and R$^4$ is CH$_3$, and R$^1$ is CH$_3$, R$^2$ is CHO, R$^3$ is CH$_3$, and R$^4$ is CH$_3$;

compositions comprising the compounds of formula [I] wherein R$^1$ is CHO, R$^2$ is H, R$^3$ is H, and R$^4$ is H, and R$^1$ is H, R$^2$ is CHO, R$^3$ is H, and R$^4$ is H, and the compounds of formula [IV] wherein R$^1$ is CHO, R$^2$ is H, R$^3$ is H, and R$^4$ is H, and R$^1$ is H, R$^2$ is CHO, R$^3$ is H, and R$^4$ is H;

compositions comprising the compounds of formula [I] wherein R$^1$ is CHO, R$^2$ is H, R$^3$ is H, and R$^4$ is CH$_3$, and R$^1$ is H, R$^2$ is CHO, R$^3$ is H, and $R^4$ is $CH_3$, and the compounds of formula [IV] wherein $R^1$ is CHO, $R^2$ is H, $R^3$ is H, and $R^4$ is $CH_3$, and $R^1$ is H, $R^2$ is CHO, $R^3$ is H, and $R^4$ is $CH_3$;

compositions comprising the compounds of formula [I] wherein $R^1$ is CHO, $R^2$ is H, $R^3$ is $CH_3$, and $R^4$ is H, and $R^1$ is H, $R^2$ is CHO, $R^3$ is $CH_3$, and $R^4$ is H, and the compounds of formula [IV] wherein $R^1$ is CHO, $R^2$ is H, $R^3$ is $CH_3$, and $R^4$ is H, and $R^1$ is H, $R^2$ is CHO, $R^3$ is $CH_3$, and $R^4$ is H;

compositions comprising the compounds of formula [I] wherein $R^1$ is CHO, $R^2$ is H, $R^3$ is $CH_3$, and $R^4$ is $C_3$, and $R^1$ is H, $R^2$ is CHO, $R^3$ is $CH_3$, and $R^4$ is $CH_3$, and the compounds of formula [IV] wherein $R^1$ is CHO, $R^2$ is H, $R^3$ is $CH_3$, and $R^4$ is $CH_3$, and R1 is H, $R^2$ is CHO, $R^3$ is $CH_3$, and $R^4$ is $CH_3$;

compositions comprising the compounds of formula [I] wherein R is $CH_3CO$, $R^2$ is $CH_3$, is $CH_3$, and $R^4$ is H, and $R^1$ is $CH_3$, $R^2$ is $CH_3CO$, and $R^3$ is $CH_3$, and $R^4$ is H, and the compounds of formula [IV] wherein $R^1$ is $CH_3CO$, $R^2$ is $CH_3$, $R^3$ is $CH_3$, and $R^4$ is H, and $R^1$ is $CH_3$, $R^2$ is $CH_3CO$, $R^3$ is $CH_3$, and $R^4$ is H;

compositions comprising the compounds of formula [I] wherein $R^1$ is $CH_3CO$, $R^2$ is $CH_3$, $R^3$ is $CH_3$, and $R^4$ is $CH_3$, and $R^1$ is $CH_3$, $R^2$ is $CH_3CO$, $R^3$ is $CH_3$, and $R^4$ is $CH_3$, and the compounds of formula [IV] wherein $R^1$ is $CH_3CO$, $R^2$ is $CH_3$, $R^3$ is $CH_3$, and $R^4$ is $CH_3$, and $R^1$ is $CH_3$, $R^2$ is $CH_3CO$, $R^3$ is $CH_3$, and $R^4$ is $CH_3$;

compositions comprising the compounds of formula [I] wherein $R^1$ is $CH_3CO$, $R^2$ is $CH_3$, $R^3$ is H, and $R^4$ is $CH_3$, and $R^1$ is $CH_3$, $R^2$ is $CH_3CO$, $R^3$ is H, and $R^4$ is $CH_3$, and the compounds of formula [IV] wherein $R^1$ is $CH_3CO$, $R^2$ is $CH_3$, $R^3$ is H, and $R^4$ is $CH_3$, and $R^1$ is $CH_3$, $R^2$ is $CH_3CO$, $R^3$ is H, and $R^4$ is $CH_3$;

compositions comprising the compounds of formula [I] wherein $R^1$ is $CH_3CO$, $R^2$ is H, $R^3$ is $CH_3$, and $R^4$ is H, and $R^1$ is H, $R^2$ is $CH_3CO$, $R^3$ is $CH_3$, and $R^4$ is H, and the compounds of formula [IV] wherein $R^1$ is $CH_3CO$, $R^2$ is H, $R^3$ is $CH_3$, and $R^4$ is H, and $R^1$ is H, $R^2$ is $CH_3CO$, $R^3$ is $CH_3$, and $R^4$ is H;

compositions comprising the compounds of formula [I] wherein $R^1$ is $CH_3CO$, $R^2$ is H, $R^3$ is $CH_3$, and $R^4$ is $CH_3$, and $R^1$ is H, $R^2$ is $CH_3CO$, $R^3$ is $CH_3$, and $R^4$ is $CH_3$, and the compounds of formula [IV] wherein $R^1$ is $CH_3CO$, $R^2$ is H, $R^3$ is $CH_3$, and $R^4$ is $CH_3$, and $R^1$ is H, $R^2$ is $CH_3CO$, $R^3$ is $CH_3$, and $R^4$ is $CH_3$;

compositions comprising the compounds of of formula [I] wherein $R^1$ is $CH_3$, $R^2$ is CHO, $R^3$ is H, and $R^4$ is H, and $R^1$ is CHO, $R^2$ is $CH_3$, $R^3$ is H, and $R^4$ is H, and the compounds of formula [IV] wherein $R^1$ is $CH_3$, $R^2$ is CHO, $R^3$ is H, and $R^4$ is H, and $R^1$ is CHO, $R^2$ is $CH_3$, $R^3$ is H, and $R^4$ is H;

compositions comprising the compounds of of formula [I] wherein $R^1$ is $CH_3$, $R^2$ is CHO, $R^3$ is H, and $R^4$ is $CH_3$, and $R^1$ is CHO, $R^2$ is $CH_3$, $R^3$ is H, and $R^4$ is $CH_3$, and the compounds of formula [IV] wherein $R^1$ is $CH_3$, $R^2$ is CHO, $R^3$ is H, and $R^4$ is $CH_3$, and $R^1$ is CHO, $R^2$ is $CH_3$, $R^3$ is H, and $R^4$ is $CH_3$;

compositions comprising the compounds of formula [I] wherein $R^1$ is $CH_3$, $R^2$ is CHO, $R^3$ is $CH_3$, and $R^4$ is H, and $R^1$ is CHO, $R^2$ is $CH_3$, $R^3$ is $CH_3$, and $R^4$ is H, and the compounds of formula [IV] wherein $R^1$ is $CH_3$, $R^2$ is CHO, $R^3$ is $CH_3$, and $R^4$ is H, and $R^1$ is CHO, $R^2$ is $CH_3$, $R^3$ is $CH_3$, and $R^4$ is H;

compositions comprising the compounds of formula [I] wherein $R^1$ is $CH_3$, $R^2$ is CHO, $R^3$ is $CH_3$, and $R^4$ is $CH_3$, and $R^1$ is CHO, $R^2$ is $CH_3$, $R^3$ is $CH_3$, and $R^4$ is $CH_3$, and the compounds of formula [IV] wherein $R^1$ is $CH_3$, $R^2$ is CHO, $R^3$ is $CH_3$, and $R^4$ is $CH_3$, and $R^1$ is CHO, $R^2$ is $CH_3$, $R^3$ is $CH_3$, and $R^4$ is $CH_3$;

compositions comprising the compounds of formula [I] wherein $R^1$ is H, $R^2$ is CHO, $R^3$ is H, and $R^4$ is H, and $R^1$ is CHO, $R^2$ is H, $R^3$ is H, and $R^4$ is H, and the compounds of formula [IV] wherein $R^1$ is H, $R^2$ is CHO, $R^3$ is H, and $R^4$ is H, and $R^1$ is CHO, $R^2$ is H, $R^3$ is H, and $R^4$ is H;

compositions comprising the compounds of formula [I] wherein $R^1$ is H, $R^2$ is CHO, $R^3$ is H, and $R^4$ is $CH_3$, and $R^1$ is CHO, $R^2$ is H, $R^3$ is H, and $R^4$ is $CH_3$, and the compounds of formula [IV] wherein $R^1$ is H, $R^2$ is CHO, $R^3$ is H, and $R^4$ is $CH_3$, and $R^1$ is CHO, $R^2$ is H, $R^3$ is H, and $R^4$ is $CH_3$;

compositions comprising the compounds of formula [I] wherein R is H, $R^2$ is CHO, $R^3$ is $CH_3$, and $R^4$ is H, and $R^1$ is CHO, $R^2$ is H, $R^3$ is $CH_3$, and $R^4$ is H, and the compounds of formula [IV] wherein $R^1$ is H, $R^2$ is CHO, $R^3$ is $CH_3$, and $R^4$ is H, and $R^1$ is CHO, $R^2$ is H, $R^3$ is $CH_3$, and $R^4$ is H; and compositions comprising the compounds of formula [I] wherein $R^1$ is H, $R^2$ is CHO, $R^3$ is $CH_3$, and $R^4$ is $CH_3$, and $R^1$ is CHO, $R^2$ is H, $R^3$ is $CH_3$, and $R^4$ is $CH_3$, and the compounds of formula [IV] wherein $R^1$ is H, $R^2$ is CHO, $R^3$ is $CH_3$, and $R^4$ is $CH_3$, and $R^1$ is CHO, $R^2$ is H, $R^3$ is $CH_3$, and $R^4$ is $CH_3$; and compositions comprising the compounds of formula [I] wherein $R^1$ is $CH_3$, $R^2$ is $CH_3CO$, $R^3$ is H, and $R^4$ is $CH_3$, and $R^1$ is $CH_3CO$, $R^2$ is $CH_3$, $R^3$ is H, and $R^4$ is $CH_3$, and the compounds of formula [IV] wherein $R^1$ is $CH_3$, $R^2$ is $CH_3CO$, $R^3$ is H, and $R^4$ is $CH_3$, and $R^1$ is $CH_3CO$, $R^2$ is $CH_3$, $R^3$ is H, and $R^4$ is $CH_3$.

compositions comprising the compounds of formula [I] wherein $R^1$ is H, $R^2$ is $CH_3CO$, $R^3$ is $CH_3$, and $R^4$ is H, and $R^1$ is $CH_3CO$, $R^2$ is H, $R^3$ is $CH_3$, and $R^4$ is H, and the compounds of formula [IV] wherein $R^1$ is H, $R^2$ is $CH_3CO$, $R^3$ is $CH_3$, and $R^4$ is H, and $R^1$ is $CH_3CO$, $R^2$ is H, $R^3$ is $CH_3$, and $R^4$ is H.

compositions comprising the compounds of formula [I] wherein $R^1$ is H, $R^2$ is $CH_3CO$, $R^3$ is $CH_3$, and $R^4$ is $CH_3$, and $R^1$ is $CH_3CO$, $R^2$ is H, $R^3$ is $CH_3$, and $R^4$ is $CH_3$, and the compounds of formula [IV] wherein $R^1$ is H, $R^2$ is $CH_3CO$, $R^3$ is $CH_3$, and $R^4$ is $CH_3$, and $R^1$ is $CH_3CO$, $R^2$ is H, $R^3$ is $CH_3$, and $R^4$ is $CH_3$.

compositions comprising the compounds of formula [I] wherein $R^1$ is $CH_3CO$, $R^2$ is H, $R^3$ is H, and $R^4$ is $CH_3$, and $R^1$ is H, $R^2$ is $CH_3CO$, $R^3$ is H, and $R^4$ is $CH_3$, and the compounds of formula [IV] wherein $R^1$ is $CH_3CO$, $R^2$ is H, $R^3$ is H, and $R^4$ is $CH_3$, and $R^1$ is H, $R^2$ is $CH_3CO$, $R^3$ is H, and $R^4$ is $CH_3$.

compositions comprising the compounds of formula [I] wherein $R^1$ is H, $R^2$ is $CH_3CO$, $R^3$ is H, and $R^4$ is $CH_3$, and $R^1$ is $CH_3CO$, $R^2$ is H, $R^3$ is H, and $R^4$ is $CH_3$, and the compounds of formula [IV] wherein $R^1$ is H, $R^2$ is $CH_3CO$, $R^3$ is H, and $R^4$ is $CH_3$, and $R^1$ is $CH_3CO$, $R^2$ is H, $R^3$ is H, and $R^4$ is $CH_3$.

The formylated and acetylated tetramethyl and pentamethyl isopropyl indane compounds and compositions thereof have high utility in the fragrance industry. These compounds or compositions can be used alone or in combination with one or more ingredients to provide a sweet, musky fragrance. Compounds particularly suited for use in combination with the novel isopropyl indanes of the invention include 7-formyl- or 7-acetyl-1,1,3,4, 4,6-hexamethyl-1,2,3,4-tetrahydronaphthalene. Such compounds can be prepared using well-known methodology such as that disclosed in U.S. Pat. Nos. 4,877,910, 4,877,911, 4,877,912, 4,877,913, 4,877,914, 4,877,915, 4,877,916, 3,856,875, 3,246,044, 4,284,818, 3,379,785, and 4,551,573, Japanese Patent Publication SHO 57-40420, *Organic Synthesis*, Collective Vol. 5, pp. 49–50 (John Wiley & Sons, 1973) and U.S. Pat. Nos. 4,446,908, 4,352,748, 2,752,404, 2,759,022, and 2,851,501. Each of the foregoing documents is incorporated herein by reference in their entirety.

The acylated indane compounds and compositions of the invention may be used as olfactory components in anionic, cationic, nonionic and zwitterionic detergents, soaps, fabric softener compositions, fabric softener articles for use in clothes dryers, space odorants and deodorants, perfumes, colognes, toilet water, bath preparations, deodorants, cosmetics, hand lotions, sunscreens, powders, as well as in other ways. The amount of the acylated isopropyl indanes to be used in augmenting or enhancing the aroma of an article or composition will vary depending upon the particular use and particular indane employed, as will be readily apparent to those skilled in the art. However, the compounds are generally employed in an amount of about 0.05 percent by weight of the perfumed article up to about 30 percent by weight of the perfumed article.

In addition, the perfumed composition or fragrance composition of the invention can contain a vehicle or carrier. Such vehicles or carriers include liquids such as a non-toxic alcohol, a non-toxic glycol, or the like. An example of a non-toxic alcohol is ethyl alcohol. An example of a non-toxic glycol is 1,2-propylene glycol. Alternatively, the vehicle or carrier can be an absorbent solid such as a gum, e.g., gum arabic, xantham gum or guar gum, or components for encapsulating a composition such as gelatin, by means of coacervation or such as a urea formaldehyde polymer whereby a polymeric shell is formed around a liquid perfume oil center. The amount of the vehicle or carrier will vary depending upon the particular use intended, as will be readily apparent to those skilled in the art. However, the vehicle or carrier can generally be employed in an amount of about 5 percent by weight up to about 95 percent by weight of the preferred composition.

The present invention is further described in the following Examples. These Examples are not to be construed as limiting the scope of the appended Claims.

In each Example, the reaction flasks were equipped with a condenser, mechanical stirrer, addition funnel and thermocouple/temperature controller connected to an automatic laboratory jack. The flasks were cooled, when necessary, with a dry ice/isopropanol bath. The flask contents were continuously stirred throughout the reaction.

Results were analyzed on both polar and non-polar gas chromatography columns. All gas chromatography analyses were carried on capillary columns using a weight percent internal standard method of analysis. Structural identifications were assigned based on GCMS fragmentation patterns compared to standards.

Examples 1 through 3 are examples of processes of the preparation of unformylated and unacetylated isopropyl indane compositions which can then be formylated or acetylated using conventional technology to produce a composition of the present invention. Example 4 is an example of the preparation of a formylated isopropyl indane composition of the invention.

EXAMPLES

EXAMPLE 1

A 100 ml four-necked round bottom flask was charged with 1,1,3,4,4,6-hexamethyl-1,2,3,4-tetrahydronaphthalene (HMT) (20.0 g) and dichloromethane (32.6 g) and cooled to 0° C. with a dry ice/isopropanol bath. To the flask was then added, with stirring, anhydrous $AlCl_3$ (2.507 g; 20.3 mole percent $AlCl_3$ based on the amount of HMT charged). The temperature of the flask was maintained between about 0° C. and about 10° C. while the reaction was allowed to proceed for about 2.5 hours. The reaction was then quenched with ice water (25 ml), and the resultant product washed with deionized water. The aqueous layer was extracted twice with ether, the organics were combined, dried over $K_2CO_3$, and rotoevaporated to yield a crude product (18.26 g) containing 37.32 weight percent of a mixture of 1,1,3,5-tetramethyl-3-isopropylindane and 1,3,3,5-tetramethyl-1-isopropylindane, and 41.55 weight percent of a mixture of 1,1,3,4,4,6-hexamethyl-1,2,3,4-tetrahydronaphthalene and 1,1,2,4,4,6-hexamethyl-1,2,3,4-tetrahydronaphthalene.

EXAMPLE 2

A 25 ml three-necked round bottom flask was charged with 1,1,3,4,4,6-hexamethyl-1,2,3,4-tetrahydronaphthalene (HMT) (5.02 g) and dichloromethane (8.16 g) and cooled to 0° C. To the flask was then added $AlCl_3$ (0.625 g; 20.2 mole percent $AlCl_3$ based on the amount of HMT charged). The temperature of the flask was maintained at about 0° C. while the reaction was allowed to proceed for about 5 hours. The reaction was then quenched with ice water (10 ml), the aqueous layer was extracted twice with ether, and the resultant product was washed with deionized water. The organics were combined, dried over $K_2CO_3$, and rotoevaporated to yield a crude product (4.21 g) containing 36.56 weight percent of a mixture of 1,1,3,5-tetramethyl-3-isopropylindane and 1,3,3,5-tetramethyl-1-isopropylindane, and 45.95 weight percent of a mixture of 1,1,3,4,4,6-hexamethyl-1,2,3,4-tetrahydronaphthalene and 1,1,2,4,4,6-hexamethyl-1,2,3,4-tetrahydronaphthalene.

EXAMPLE 3

A 25 ml three-necked round bottom flask was charged with cyclohexane (4.83 g) and 1,1,3,4,4,6-hexamethyl-1,2,3,4-tetrahydronaphthalene (HMT) (5.03 g) and cooled to 10° C. with a dry ice/isopropanol bath.

To the flask was then added, with stirring, methyltrioctylammonium chloride (0.47 g). Next, anhydrous AlCl₃ (1.54 g; 50 mole percent AlCl₃ based on the amount of HMT charged) was added and the reaction was allowed to proceed for about 2 hours during which time the temperature of the flask was maintained at about 10° C. The reaction was then quenched over ice (50 ml), and the layers were separated. The aqueous portion was extracted twice with dichloromethane (75 ml per extraction), the organics were combined, and the resultant product washed with deionized water and dried over K₂CO₃ to yield a crude product (5.25 g) after rotoevaporation containing 43.52 weight percent of a mixture of 1,1,3,5-tetramethyl-3-isopropylindane and 1,3,3,5-tetramethyl-3-isopropylindane, and 41.81 weight percent of a mixture of 1,1,3,4,4,6-hexamethyl-1,2,3,4-tetrahydronaphthalene and 1,1,2,4,4,6-hexamethyl-1,2,3,4-tetrahydronaphthalene.

EXAMPLE 4

A 500 ml 3-necked round bottom flask was charged with a 20.6 g mixture of 1,1,3,5-tetramethyl-3-isopropylindane and 1,3,3,5-tetramethyl-1-isopropylindane (36.8 weight percent combined indanes) and 1,1,3,4,4,6-hexamethyl-1,2,3,4-tetrahydronaphthalene and 1,1,2,4,4,6-hexamethyl-tetrahydronaphthalene (41.7 weight percent combined tetralins), the mixture being prepared substantially in accordance with the procedures of Example 1. To the flask was then added dichloromethane (115 ml) under a nitrogen gas. The flask was cooled to about 5° C. to about 10° C. with a dry ice/isopropanol bath. Titanium tetrachloride (18.3 ml) was added by syringe to the flask over a period of about 5 minutes. The temperature was then stabilized at about 5° C. and 2,2-dichloromethyl methyl ether (7.5 ml) was added over a period of about 25 minutes. After this addition was completed, the addition funnel was rinsed with dichloromethane (5 ml). The reaction was stirred for about 5 additional minutes while maintaining a temperature of about 5° C. The flask was then heated using a warm water bath to a temperature of about 20° C. for about 30 minutes, and then heated to a temperature of about 35° C. for about 15 minutes. Using a dry ice/isopropanol bath, the flask was then cooled down to about 4° C., at which time water (150 ml) was added over about a 20 minute period. The resultant product was then worked up using the procedures described in *Organic Synthesis*, Collective Vol. 5, pp. 49–50 (John Wiley & Sons, 1973). The process yielded a crude product (24.89 g) containing 20.69 weight percent of a mixture of 7-formyl-1,1,3,5-tetramethyl-3-isopropylindane and 7-formyl-1,3,3,5-tetramethyl-1-isopropylindane, and 24.1 weight percent of a mixture of 7-formyl-1,1,3,4,4,6-hexamethyl-1,2,3,4-tetrahydronaphthalene and 7-formyl-1,1,2,4,4,6-hexamethyl-1,2,3,4-tetrahydronaphthalene.

Various modifications of the invention, in addition to those shown and described herein, will be apparent to those skilled in the art from the foregoing description. Such modifications are also intended to fall within the scope of the appended Claims.

What is claimed is:

1. A compound of the formula:

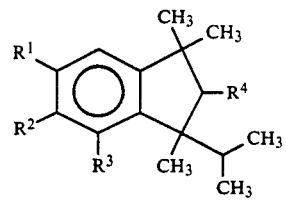

wherein:
$R^1$ is H, CH₃, CHO, or CH₃CO;
$R^2$ is H, CH₃, CHO, or CH₃CO;
$R^3$ is H, or CH₃; and
$R^4$ is H, or CH₃;
provided that
(i) one of $R^1$ or $R^2$ is CHO, or CH₃CO;
(ii) one of $R^1$ or $R^2$ is H, or CH₃;
(iii) when $R^3$ and $R^4$ are both H, $R^1$ and $R^2$ are other than CH₃CO; and
(iv) when $R^1$ and $R^3$ are both CH₃, $R^2$ is CHO.

2. The compound of claim 1 wherein $R^1$ is CHO, $R^2$ is CH₃, $R^3$ is H, and $R^4$ is H.

3. The compound of claim 1 wherein $R^1$ is CHO, $R^2$ is CH₃, $R^3$ is CH₃, and $R^4$ is H.

4. The compound of claim 1 wherein $R^1$ is CHO, $R^2$ is CH₃, $R^3$ is H, and $R^4$ is CH₃.

5. The compound of claim 1 wherein $R^1$ is CHO, $R^2$ is H, $R^3$ is CH₃, and $R^4$ is H.

6. The compound of claim 1 wherein $R^1$ is CH₃CO, $R^2$ is CH₃, $R^3$ is CH₃, and $R^4$ is H.

7. The compound of claim 1 wherein $R^1$ is CH₃CO, $R^2$ is CH₃, $R^3$ is H, and $R^4$ is CH₃.

8. The compound of claim 1 wherein $R^1$ is CH₃, $R^2$ is CHO, $R^3$ is H, and $R^4$ is H.

9. The compound of claim 1 wherein $R^1$ is CH₃, $R^2$ is CHO, $R^3$ is CH₃, and $R^4$ is H.

10. The compound of claim 1 wherein $R^1$ is CH₃, $R^2$ is CHO, $R^3$ is H, and $R^4$ is CH₃.

11. The compound of claim 1 wherein $R^1$ is H, $R^2$ is CHO, $R^3$ is CH₃, and $R^4$ is H.

12. The compound of claim 1 wherein $R^1$ is CH₃, $R^2$ is CH₃CO, $R^3$ is H, and $R^4$ is CH₃.

13. A composition comprising a compound of claim 1 in combination with at least one compound selected from the group consisting of:
compounds of the formula

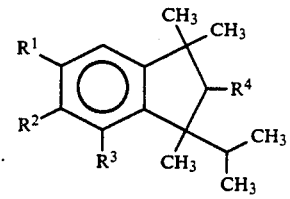

wherein
$R^1$ is H, CH₃, CHO, or CH₃CO;
$R^2$ is H, CH₃, CHO, or CH₃CO;
$R^3$ is H, or CH₃; and
$R^4$ is H, or CH₃;
provided that
(i) one of $R^1$ or $R^2$ is CHO, or CH₃CO;
(ii) one of $R^1$ or $R^2$ is H, or CH₃;
(iii) when $R^3$ and $R^4$ are both H, $R^1$ and $R^2$ are other than CH₃CO; and
(iv) when $R^1$ and $R^3$ are both CH₃, $R^2$ is CHO; and compounds of the formula

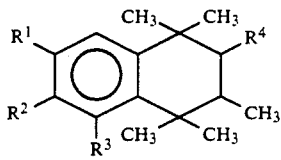

wherein
R¹ is H, CH₃, CHO, or CH₃CO;
R² is H, CH₃, CHO, or CH₃CO;
R³ is H, or CH₃; and
R⁴ is H, or CH₃;
provided that
(i) one of R¹ or R² is CHO, or CH₃CO;
(ii) one of R¹ or R² is H, or CH₃;
(iii) when R³ and R⁴ are both H, R¹ and R² are other than CH₃CO; and
(iv) when R¹ and R³ are both CH₃, R² is CHO.

14. A composition comprising the compound of claim 2 in combination with at least one compound selected, from the group consisting of:
the compound of the formula

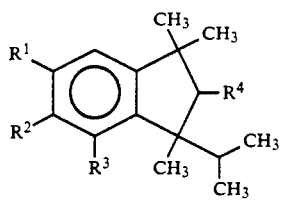

wherein R¹ is CH₃, R² is CHO, R³ is H, and R⁴ is H; and
the compounds of the formula

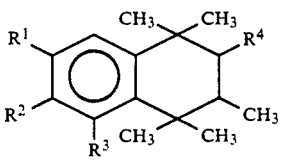

wherein R¹ is CHO, R² is CH₃, R³ is H, and R⁴ is H, and R¹ is CH₃, R² is CHO, R³ is H, and R⁴ is H.

15. A composition comprising the compound of claim 3 in combination with at least one compound selected from the group consisting of:
the compound of the formula

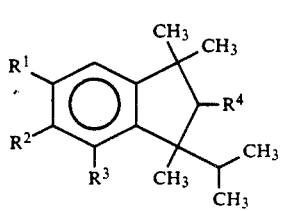

wherein R¹ is CH₃, R² is CHO, R³ is CH₃, and R⁴ is H; and
the compounds of the formula

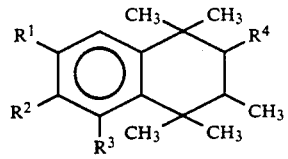

wherein R¹ is CHO, R² is CH₃, R³ is CH₃, and R⁴ is H, and R¹ is CH₃, R² is CHO, R³ is CH₃, and R⁴ is H.

16. A composition comprising the compound of claim 4 in combination with at least one compound selected from the group consisting of:
the compound of the formula

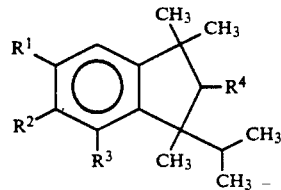

wherein R¹ is CH₃, R² is CHO, R³ is H, and R⁴ is CH₃; and
the compounds of the formula

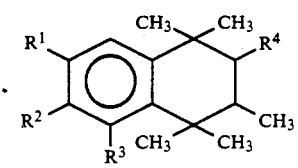

wherein R¹ is CHO, R² is CH₃, R³ is H, and R⁴ is CH₃, and R¹ is CH₃, R² is CHO, R³ is H, and R⁴ is CH₃.

17. A composition comprising the compound of claim 5 in combination with at least one compound selected from the group consisting of:
the compound of the formula

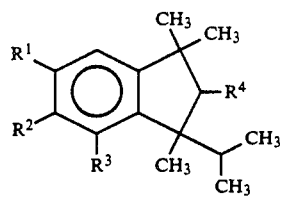

wherein R¹ is H, R² is CHO, R³ is CH₃, and R⁴ is H; and
the compounds of the formula

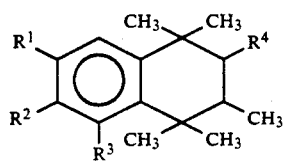

wherein R¹ is CHO, R² is H, R³ is CH₃, and R⁴ is H, and R¹ is H, R² is CHO, R³ is CH₃, and R⁴ is H.

18. A composition comprising the compound of claim 6 in combination with at least one compound selected from the group consisting of:

the compound of the formula

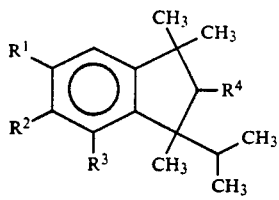 [I]

wherein R¹ is CH₃, R² is CH₃CO, R³ is CH₃, and R⁴ is H; and
the compounds of the formula

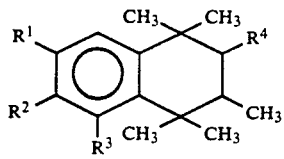 [IV]

wherein R¹ is CH₃CO, R² is CH₃, R³ is CH₃, and R⁴ is H, and R¹ is CH₃, R² is CH₃CO, R³ is CH₃, and R⁴ is H.

19. A composition comprising the compound of claim 7 in combination with at least one compound selected from the group consisting of:
the compound of the formula

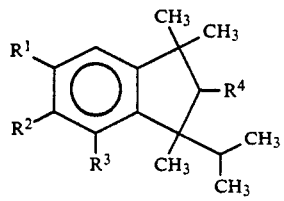 [I]

wherein R¹ is CH₃, R² is CH₃CO, R³ is H, and R⁴ is CH₃; and
the compounds of the formula

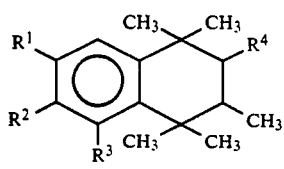 [IV]

wherein R¹ is CH₃CO, R² is CH₃, R³ is H, and R⁴ is CH₃, and R¹ is CH₃, R² is CH₃CO, R³ is H, and R⁴ is CH₃.

20. A composition comprising the compound of claim 8 in combination with at least one compound selected from the group consisting of:
the compound of the formula

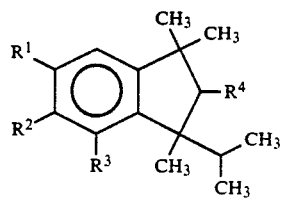 [I]

wherein R¹ is CHO, R² is CH₃, R³ is H, and R⁴ is H; and
the compounds of the formula

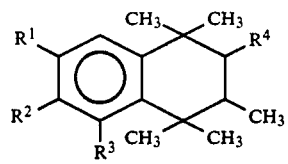 [IV]

wherein R¹ is CH₃, R² is CHO, R³ is H, and R⁴ is H, and R¹ is CHO, R² is CH₃, R³ is H, and R⁴ is H.

21. A composition comprising the compound of claim 9 in combination with at least one compound selected from the group consisting of:
the compound of the formula

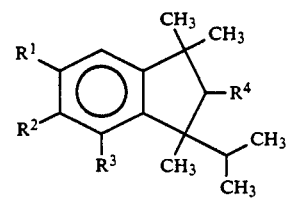 [I]

wherein R¹ is CHO, R² is CH₃, R³ is CH₃, and R⁴ is H; and
the compounds of the formula

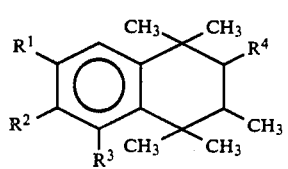 [IV]

wherein R¹ is CH₃, R² is CHO, R³ is CH₃, and R⁴ is H, and R¹ is CHO, R² is CH₃, R³ is CH₃, and R⁴ is H.

22. A composition comprising the compound of claim 10 in combination with at least one compound selected from the group consisting of:
the compound of the formula

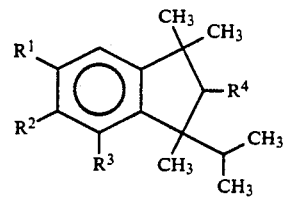 [I]

wherein R¹ is CHO, R² is CH₃, R³ is H, and R⁴ is CH₃; and
the compounds of the formula

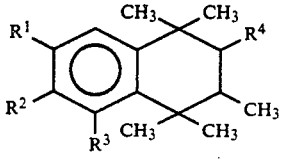 [IV]

wherein R¹ is CH₃, R² is CHO, R³ is H, and R⁴ is CH₃, R¹ is CHO, R² is CH₃, R³ is H, R⁴ is CH₃.

23. A composition comprising the compound of claim 11 in combination with at least one compound selected from the group consisting of:

the compound of the formula

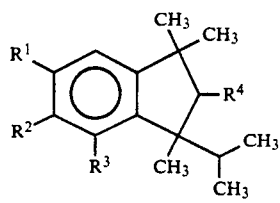

[I]

wherein $R^1$ is CHO, $R^2$ is H, $R^3$ is CH$_3$, $R^4$ is H; and the compounds of the formula

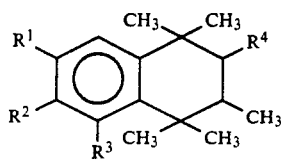

[IV]

wherein $R^1$ is H, $R^2$ is CHO, $R^3$ is CH$_3$, and $R^4$ is H, and $R^1$ is CHO, $R^2$ is H, $R^3$ is CH$_3$, and $R^4$ is H.

24. A composition comprising the compound of claim 12 in combination with at least one compound selected from the group consisting of:

the compound of the formula

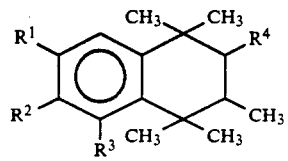

[I]

wherein $R^1$ is CH$_3$CO, $R^2$ is CH$_3$, $R^3$ is H, and $R^4$ is CH$_3$; and the compounds of the formula

[IV]

wherein $R^1$ is CH$_3$, $R^2$ is CH$_3$CO, $R^3$ is H, and $R^4$ is CH$_3$, and $R^1$ is CH$_3$CO, $R^2$ is CH$_3$, $R^3$ is H, and $R^4$ is CH$_3$.

* * * * *